(12) United States Patent
Royer et al.

(10) Patent No.: US 12,296,120 B2
(45) Date of Patent: May 13, 2025

(54) MEDICAL BALLOON

(71) Applicant: BOSTON SCIENTIFIC SCIMED, INC., Maple Grove, MN (US)

(72) Inventors: Adam Joseph Royer, Brooklyn Park, MN (US); Robert N. Squire, Maple Grove, MN (US); Daniel Lee Krautkremer, Plymouth, MN (US); Jeffrey S. Lindquist, Maple Grove, MN (US); Daniel James Horn, Shoreview, MN (US); Katherine M. Prindle, Robbinsdale, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 639 days.

(21) Appl. No.: 17/517,213

(22) Filed: Nov. 2, 2021

(65) Prior Publication Data

US 2022/0054804 A1 Feb. 24, 2022

Related U.S. Application Data

(63) Continuation of application No. 15/484,922, filed on Apr. 11, 2017, now Pat. No. 11,191,930.
(Continued)

(51) Int. Cl.
*A61M 25/10* (2013.01)
*A61M 25/00* (2006.01)

(52) U.S. Cl.
CPC .... *A61M 25/1002* (2013.01); *A61M 25/0026* (2013.01); *A61M 25/1029* (2013.01);
(Continued)

(58) Field of Classification Search
CPC .......... A61M 25/1002; A61M 25/0026; A61M 25/1029; A61M 25/1034; A61M 25/104;
(Continued)

(56) References Cited

U.S. PATENT DOCUMENTS 3,023,982 A 3/1962 Huch
4,327,736 A 5/1982 Inoue
(Continued)

FOREIGN PATENT DOCUMENTS

EP 0540858 A1 5/1993
EP 0553960 A1 8/1993
(Continued)

OTHER PUBLICATIONS

International Search Report and Written Opinion dated Jun. 28, 2017 for International Application No. PCT/US2017/027032.

*Primary Examiner* — George R Koch
*Assistant Examiner* — Christopher C Caillouet
(74) *Attorney, Agent, or Firm* — Seager, Tufte & Wickhem LLP

(57) ABSTRACT

Medical devices and methods for making and using medical devices are disclosed. An example medical device may include a catheter. The catheter may include a catheter shaft and a balloon. The balloon may comprise a cone portion, a waist portion, and a body portion. A fiber braid may be disposed along the balloon. An inner surface of the waist portion may be thermally bonded to an outer surface of the catheter shaft and an inner surface of the fiber braid may be adhesively bonded to an outer surface of the waist portion.

19 Claims, 21 Drawing Sheets

Related U.S. Application Data

(60) Provisional application No. 62/321,394, filed on Apr. 12, 2016.

(52) U.S. Cl.
CPC ...... *A61M 25/1034* (2013.01); *A61M 25/104* (2013.01); *A61M 2025/1031* (2013.01); *A61M 2025/1075* (2013.01); *A61M 2025/1084* (2013.01); *A61M 2025/1088* (2013.01)

(58) Field of Classification Search
CPC .. A61M 2025/1031; A61M 2025/1075; A61M 2025/1084; A61M 2025/1088
See application file for complete search history.

(56) References Cited

U.S. PATENT DOCUMENTS

| | | |
|---|---|---|
| 4,490,421 A | 12/1984 | Levy |
| 4,706,670 A | 11/1987 | Andersen et al. |
| 4,808,465 A | 2/1989 | Vane |
| 4,896,669 A | 1/1990 | Bhate et al. |
| 4,906,244 A | 3/1990 | Pinchuk et al. |
| 4,935,190 A | 6/1990 | Tennerstedt |
| 4,950,239 A | 8/1990 | Gahara et al. |
| 4,963,313 A | 10/1990 | Noddin et al. |
| 5,026,607 A | 6/1991 | Kiezulas |
| 5,096,848 A | 3/1992 | Kawamura |
| 5,135,516 A | 8/1992 | Sahatjian et al. |
| 5,201,706 A | 4/1993 | Noguchi et al. |
| 5,250,069 A | 10/1993 | Nobuyoshi et al. |
| 5,264,260 A | 11/1993 | Saab |
| 5,267,959 A | 12/1993 | Forman |
| 5,270,086 A | 12/1993 | Hamlin |
| 5,304,121 A | 4/1994 | Sahatjian |
| 5,304,340 A | 4/1994 | Downey |
| 5,306,246 A | 4/1994 | Sahatjian et al. |
| 5,314,443 A | 5/1994 | Rudnick |
| 5,328,468 A | 7/1994 | Kaneko et al. |
| 5,330,428 A | 7/1994 | Wang et al. |
| 5,330,429 A | 7/1994 | Noguchi et al. |
| 5,344,400 A | 9/1994 | Kaneko et al. |
| 5,403,340 A | 4/1995 | Wang et al. |
| 5,407,623 A | 4/1995 | Zachariades et al. |
| 5,500,180 A | 3/1996 | Anderson et al. |
| 5,503,631 A | 4/1996 | Onishi et al. |
| 5,509,899 A | 4/1996 | Fan et al. |
| 5,556,383 A | 9/1996 | Wang et al. |
| 5,576,072 A | 11/1996 | Hostettler et al. |
| 5,578,374 A | 11/1996 | Dunbar et al. |
| 5,647,848 A | 7/1997 | Jorgensen |
| 5,693,034 A | 12/1997 | Buscemi et al. |
| 5,702,756 A | 12/1997 | Mckean et al. |
| 5,714,110 A | 2/1998 | Wang et al. |
| 5,797,877 A | 8/1998 | Hamilton et al. |
| 5,827,289 A | 10/1998 | Reiley et al. |
| 5,833,657 A | 11/1998 | Reinhardt et al. |
| 5,868,708 A | 2/1999 | Hart et al. |
| 5,913,861 A | 6/1999 | Trotta |
| 5,958,582 A | 9/1999 | Dunbar et al. |
| 6,110,483 A | 8/2000 | Whitbourne et al. |
| 6,146,356 A | 11/2000 | Wang et al. |
| 6,156,254 A | 12/2000 | Andrews et al. |
| 6,267,775 B1 | 7/2001 | Clerc et al. |
| 6,270,522 B1 | 8/2001 | Simhambhatla et al. |
| 6,306,144 B1 | 10/2001 | Sydney et al. |
| 6,416,494 B1 | 7/2002 | Wilkins |
| 6,444,324 B1 | 9/2002 | Yang et al. |
| 6,528,150 B2 | 3/2003 | Nazarova et al. |
| 6,572,813 B1 | 6/2003 | Zhang et al. |
| 6,673,053 B2 | 1/2004 | Wang et al. |
| 6,695,809 B1 | 2/2004 | Lee |
| 6,723,267 B2 | 4/2004 | Simmelink et al. |
| 6,746,425 B1 | 6/2004 | Beckham |
| 6,896,892 B2 | 5/2005 | Mount et al. |
| 7,252,650 B1 | 8/2007 | Andrews et al. |
| 7,635,510 B2 | 12/2009 | Horn et al. |
| 2003/0054090 A1 | 3/2003 | Hansen |
| 2003/0106346 A1 | 6/2003 | Matsumoto |
| 2003/0139798 A1 | 7/2003 | Brown et al. |
| 2003/0149399 A1* | 8/2003 | Langan ............. A61M 25/10 604/533 |
| 2004/0006359 A1 | 1/2004 | Laguna |
| 2004/0058603 A1 | 3/2004 | Hayes |
| 2004/0082965 A1 | 4/2004 | Beckham |
| 2004/0098120 A1 | 5/2004 | Williams et al. |
| 2004/0109964 A1 | 6/2004 | Beckham |
| 2006/0008606 A1 | 1/2006 | Horn et al. |
| 2007/0106216 A1 | 5/2007 | Noddin |
| 2009/0012610 A1 | 1/2009 | Olson et al. |
| 2009/0099517 A1 | 4/2009 | Steadham |
| 2010/0010438 A1 | 1/2010 | Simpson |
| 2010/0057001 A1 | 3/2010 | Chen et al. |
| 2011/0046654 A1 | 2/2011 | Kuppurathanam |
| 2012/0277783 A1 | 11/2012 | Cummins et al. |
| 2012/0296363 A1 | 11/2012 | Davies, Jr. et al. |
| 2013/0048200 A1 | 2/2013 | Pepper et al. |
| 2013/0131709 A1 | 5/2013 | Davies, Jr. et al. |
| 2013/0255866 A1 | 10/2013 | Beckham |
| 2014/0066896 A1 | 3/2014 | Tilson et al. |
| 2014/0166152 A1 | 6/2014 | Graves et al. |
| 2014/0166193 A1 | 6/2014 | Pepper et al. |
| 2014/0182738 A1 | 7/2014 | Simpson |
| 2014/0243874 A1 | 8/2014 | Pepper et al. |
| 2015/0081006 A1 | 3/2015 | Chuter et al. |
| 2015/0141917 A1 | 5/2015 | Tilson et al. |
| 2015/0209556 A1 | 7/2015 | Timothy |
| 2015/0297871 A1 | 10/2015 | Aggerholm et al. |
| 2017/0043119 A1 | 2/2017 | Kubo et al. |
| 2017/0291014 A1 | 10/2017 | Royer et al. |

FOREIGN PATENT DOCUMENTS

| | | |
|---|---|---|
| EP | 1388346 A1 | 2/2004 |
| EP | 1189553 B1 | 3/2004 |
| JP | 2009513299 A | 4/2009 |
| WO | 9803218 A1 | 1/1998 |
| WO | 0100109 A1 | 1/2001 |
| WO | 2004028407 A1 | 4/2004 |
| WO | 2004050140 A2 | 6/2004 |
| WO | 2010051488 A1 | 5/2010 |

* cited by examiner

MEDICAL BALLOON

CROSS REFERENCE TO RELATED APPLICATIONS

This application is a continuation of U.S. patent application Ser. No. 15/484,922, filed Apr. 11, 2017, which claims the benefit of priority under 35 U.S.C. § 119 to U.S. Provisional Application Ser. No. 62/321,394, filed Apr. 12, 2016, the entirety of which are incorporated herein by reference.

TECHNICAL FIELD

The invention relates to intravascular medical devices such as medical balloons and methods of making the same.

BACKGROUND

Medical balloons can be used to administer a variety of treatments. For example, in an angioplasty procedure, a balloon can be used to widen a constricted bodily vessel, such as a coronary artery. A balloon can also be used to deliver a tubular member, such as a stent, that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an increase in the rate of blood flow. After use, the balloon is collapsed and withdrawn.

In stent delivery, the stent is compacted on the balloon and transported to a target site. Upon reaching the site, the balloon can be expanded to deform and to fix the stent at a predetermined position, e.g., in contact with the vessel wall. The balloon can then be collapsed and withdrawn.

Medical balloons can be manufactured by extruding a cylindrical tube of polymer and then pressurizing the tube while heating to expand the tube into the shape of a balloon. The balloon can be fastened around the exterior of a hollow catheter shaft to form a balloon catheter. The hollow interior of the balloon is in fluid communication with the hollow interior of the shaft. The shaft may be used to provide a fluid supply for inflating the balloon or a vacuum for deflating the balloon.

SUMMARY

This disclosure provides design, material, manufacturing method, and use alternatives for medical devices. A catheter is disclosed. The catheter comprises:
a catheter shaft;
a balloon, the balloon comprising a cone portion, a waist portion, and a body portion; and
a fiber braid disposed along at least a portion of the balloon;
wherein an inner surface of the waist portion is thermally bonded to an outer surface of the catheter shaft and an inner surface of the fiber braid is adhesively bonded to an outer surface of the waist portion.

Alternatively or additionally to any of the embodiments above, further comprising a first thermoplastic polyurethane coating disposed between the fiber braid and an outer surface of the balloon.

Alternatively or additionally to any of the embodiments above, further comprising a second thermoplastic polyurethane coating along an outer surface of the fiber braid.

Alternatively or additionally to any of the embodiments above, the fiber braid includes an ultra high molecular weight polyethylene.

Alternatively or additionally to any of the embodiments above, the balloon is formed of a poly(ether-block-amide).

Alternatively or additionally to any of the embodiments above, the balloon includes an inner layer formed of a poly(ether-block-amide) and an outer layer formed of a polyamide.

Alternatively or additionally to any of the embodiments above, the catheter shaft includes a polyamide.

Alternatively or additionally to any of the embodiments above, the fiber braid is adhesively bonded to the outer surface of the waist portion of the balloon with a thermoset adhesive.

Alternatively or additionally to any of the embodiments above, the thermoset adhesive includes a moisture cure material, a UV cure material, or a combination thereof.

Alternatively or additionally to any of the embodiments above, the catheter shaft is a dual lumen catheter shaft.

A catheter is disclosed. The catheter comprises:
a polymeric catheter shaft;
a balloon having a cone portion, a waist portion, and a body portion, the balloon including a thermoplastic elastomer; and
a fiber braid disposed along the balloon, the fiber braid including molecularly oriented high molecular weight polymer;
wherein an inner surface of the waist portion is bonded to an outer surface of the polymeric catheter shaft using a first method and wherein an inner surface of the fiber braid is bonded to an outer surface of the waist portion by a second method that is different than the first method so as to preserve the molecular orientation of the molecularly oriented high molecular weight polymer of the fiber braid.

Alternatively or additionally to any of the embodiments above, the inner surface of the fiber braid is adhesive bonded to the outer surface of the waist portion.

Alternatively or additionally to any of the embodiments above, the outer surface of the polymeric catheter shaft is thermally bonded to the inner surface of the waist portion.

Alternatively or additionally to any of the embodiments above, the thermal bond between the outer surface of the polymeric catheter shaft and the inner surface of the waist portion forms an interface comprising the thermoplastic elastomer of the balloon and a polymeric material of the polymeric catheter shaft.

Alternatively or additionally to any of the embodiments above, the thermoplastic elastomer of the balloon and a polymer of the polymeric catheter shaft have a common monomer.

A method of making a catheter assembly is disclosed. The method comprises:
disposing a fiber braid about a balloon, the balloon comprising a cone portion, a waist portion and a body portion, the fiber braid being terminated distally at a predetermined point relative to the waist portion;
disposing the balloon on a catheter shaft;

applying heat to at least a portion of the waist portion to thermally bond an inner surface of the fiber braid to an outer surface of the waist portion; and adhesively bonding the inner surface of the distal portion of the fiber braid to the outer surface of the waist portion.

Alternatively or additionally to any of the embodiments above, further comprising trimming the waist portion to a predetermined length.

Alternatively or additionally to any of the embodiments above, the adhesive is applied after trimming the waist portion.

Alternatively or additionally to any of the embodiments above, wherein a first section the fiber braid is supported by the waist portion and a second section of the fiber braid extends distally beyond the waist portion such that the second section is unsupported by the waist portion, further comprising proximally retracting at least the second section of the fiber braid and a region of the first section of the fiber braid to expose at least some of the waist portion before applying an adhesive, distally moving the second section of the fiber braid after applying the adhesive, and curing the adhesive.

Alternatively or additionally to any of the embodiments above, disposing the balloon on a catheter shaft includes welding the waist portion to the catheter shaft, braiding the fiber braid over the balloon and the catheter shaft, trimming the fiber braid at a predetermined location, and applying the adhesive to the waist portion, to the inner surface of the fiber braid at the waist portion at the predetermined location, or both.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
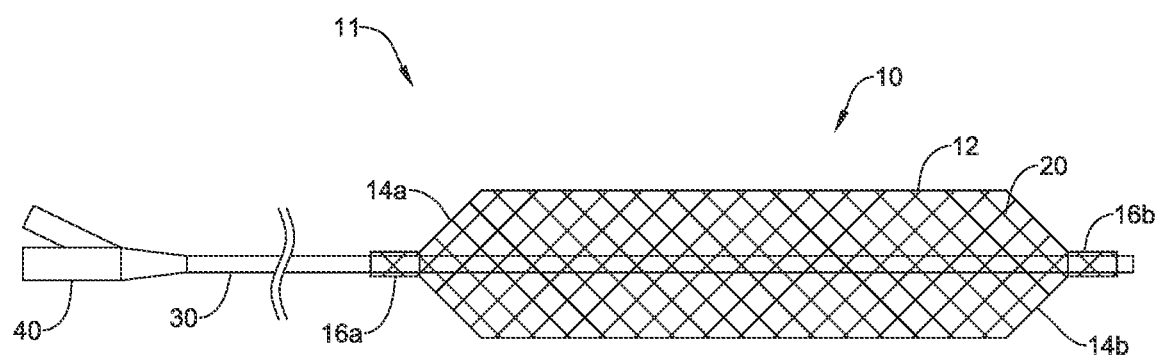
FIG. 1 is a side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As used herein, the terms "proximal" and "distal" refer to that which is closest to the user such as a surgeon and that which is furthest from the user respectively.

A side view of an exemplary balloon catheter 11 is illustrated in FIG. 1. The balloon catheter 11 may include an expandable medical balloon 10 having a fiber braid 20 disposed thereon and mounted on the distal end of a catheter shaft 30. The catheter shaft 30 extends from a manifold assembly 40 at a proximal end of the catheter shaft 30. The balloon 10 is shown having a body portion 12, a proximal cone portion 14a, a distal cone portion 14b, a proximal waist portion 16a, and a distal waist portion 16b. The balloon 10 may be secured to the catheter shaft 30 at the proximal and distal waist portions 16a and 16b, respectively.

Figure 3:
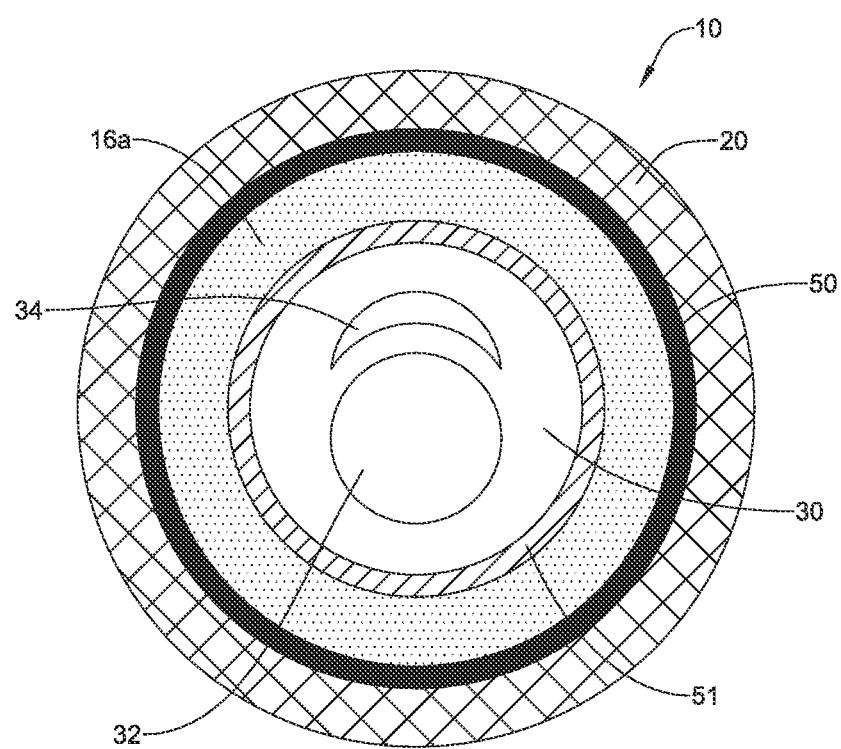
FIG. 3 is a cross-section of an example medical device taken at section 3-3 in FIG. 2.

For the balloon catheter 11 shown in FIG. 1, the catheter shaft 30 is depicted as a dual-lumen catheter shaft 30 that includes a guidewire lumen 32 for a guidewire (not shown) and an inflation lumen 34 for inflation of the balloon 10 as shown in cross-section in FIG. 3. Alternatively, the catheter shaft 30 may include an inner tubular member defining the guidewire lumen 32 and an outer tubular member extending around the inner tubular member. In these instances, the inflation lumen 34 may be defined between the inner tubular member and the outer tubular member. In such cases, the proximal waist portion 16a may be secured to a distal end region of the outer tubular member and the distal waist portion 16b may be secured to a distal end region of the inner tubular member. Other catheter shafts are contemplated.

The balloon 10 may be pre-formed, for example, by radial expansion of a tubular parison, which is optionally also longitudinally stretched. The extruded parison may be radially expanded in a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. The balloon 10 may range in size from about 4 mm to about 26 mm.

The balloon 10 may be formed from typical balloon materials including compliant, semi-compliant, and non-compliant balloon materials. These materials may include thermoplastic polymers, elastomers, and non-elastomers. Such materials may include low, linear low, medium, and high density polyethylenes, polypropylenes, and copolymers and terpolymers thereof; polyurethanes; polyesters and copolyesters; polycarbonates; polyamides; thermoplastic polyimides; polyetherimides; polyetheretherketones (PEEK) and PES (polyether sulfone); and copolymers and terpolymers thereof. Physical blends and copolymers of such materials may also be used. Examples of polyesters include, but are not limited to, polyethylene terephthalate (PET), polyethylene naphthalate (PEN), polybutylene terephthalate, and copolymers thereof. Examples of polyamides which may be used include nylon 6, nylon 64, nylon 66, nylon 610, nylon 610, nylon 612, nylon 46, nylon 9, nylon 10, nylon 11, nylon 12, and mixtures thereof. Examples of suitable polyurethanes include, but are not limited to, aromatic polyether-based thermoplastic polyurethanes (TPUs) such as those available under the tradename of Tecothane® from Thermedics; thermoplastic polyurethane elastomer available under the tradename of Pellethane®, such as Pellethane® 2363-75D from Dow Chemical Co.; and high strength engineering thermoplastic polyurethane available under the tradename of Isoplast®, such as Isoplast® 301 and 302 available from Dow Chemical Co.

In some embodiments, the balloon 10 may be formed from poly(ether-block-amide) copolymers. The polyamide/polyether block copolymers are commonly identified by the acronym PEBA (polyether block amide). The polyamide and polyether segments of these block copolymers may be linked through amide linkages, or ester linked segmented polymers (e.g., polyamide/polyether polyesters). Such polyamide/polyether/polyester block copolymers are made by a molten state polycondensation reaction of a dicarboxylic polyamide and a polyether diol. The result is a short chain polyester made up of blocks of polyamide and polyether. Polymers of this type are commercially available under the tradename of Pebax® from Arkema. Specific example are the "33" series polymers with hardness 60 and above, Shore D scale, for example, Pebax® 6333, 7033, and 7233. These polymers are made up of nylon 12 segments and poly(tetramethylene ether) segments linked by ester groups.

Polyester/polyether segmented block copolymers may also be employed herein. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol.

In some embodiments, the polyether segments of the polyester/polyether segmented block copolymers are aliphatic polyethers having at least 2 and no more than 10 linear saturated aliphatic carbon atoms between ether linkages. Ether segments may have 4-6 carbons between ether linkages, and can be poly(tetramethylene ether) segments. Examples of other polyethers which may be employed in place of or in addition to tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, such as between 650 and 1000.

In some embodiments, the polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta-, or para-phthalic acid, napthalenedicarboxylic acid, or meta-terphenyl-4,4'-dicarboxylic acids. Specific examples of polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

The above lists are intended for illustrative purposes only, and not as a limitation on the present disclosure. It is within purview of those of ordinary skill in the art to select other polymers without departing from the scope of this disclosure.

The balloon 10 may be capable of being inflated to relative high pressures. For example, the balloon 10 may be inflated to pressures up to about 20 atm or more, or up to about 25 atm or more, or up to about 30 atm or more, or up to about 40 atm or more, or up to about 45 atm or more, or up to about 50 atm or more, or about 20-50 atm, or about 25-40 atm, or about 30-50 atm. At such elevated pressures, the bond between the proximal waist portion 16a and the catheter shaft 30 (as well as the bond between the distal waist portion 16b and the catheter shaft 30) is maintained. Furthermore, the bond between the fiber braid 20 and the balloon 10 is also maintained at these elevated pressures.

In some embodiments, the balloon 10 is formed from a compliant material. In some embodiments, the balloon 10 is formed from an elastomer, such as a block copolymer elastomer. The block copolymer elastomer may be a poly(ether-block-amide) copolymer. The balloon can also be formed of layers, for example, an inner layer formed of a first polymer material and an outer layer formed from a second polymer material different than the first polymer material. For example, in some embodiments, the inner layer may be formed from an elastomeric polymer material, for example, a block copolymer elastomer, and the outer layer is formed from a non-elastomeric polymer material. In some embodiments, the inner layer is formed of a poly(ether-block-amide) copolymer; and the outer layer is formed of a polyamide.

The fiber braid 20 may be formed from a suitable polymer material. General classes of suitable fiber braid materials include, for example, polyesters, polyolefins, polyamides, polyurethanes, liquid crystal polymers, polyimides, and mixtures thereof. More specific examples include, but are not limited to, polyesters such as polyethylene terephthalate (PET), polybutylene terephthalate (PBT), and polytrimethylene terephthalate (PTT). Polyamides include nylons and aramids such as Kevlar®. Liquid crystal polymers include Vectran®. Polyolefins include ultrahigh molecular weight polyethylene, such as Dyneema® sold by DSM Dyneema BVm Heerlen, Netherlands, Spectra® fibers, sold by Honeywell, and very high density polyethylene, and polypropylene fibers. Elastomeric fibers can be used in some cases.

In some embodiments, the fiber braid 20 comprises an ultra high molecular weight polyethylene (UHMPE). Commercially available UHMPEs include, but are not limited to, Dyneema® fiber available from DSM Dyneema BVm Heerlen, Netherlands, Spectra® fiber available from Honeywell in Morristown and Pegasus UHMWPE fiber available from Pegasus Materials in Shanghai, China. The UHMWPE fibers provide excellent strength and modulus with a small filament size to provide excellent balloon coverage and maintaining a minimal profile. However, when melted, the fibers lose their high molecular orientation and consequently, may also lose their bond tensile strength at the proximal waist portion 16a and/or the distal waist portion 16b of the balloon 10 at a thermal bond interface. Additionally coatings may be optionally applied to the balloon, such as between the outer surface of the balloon and the braid, over the outer surface of the braid or both. In some embodiments, the coating includes a thermoplastic elastomer. In other instances, the coating includes a thermoplastic polyurethane. In some instances, the coating of a thermoplastic polyurethane may be applied to the balloon 10 using a suitable technique (e.g., dip coating, spray coating, rolling, or the like) prior to braiding and is also applied to the balloon/braid after braiding.

The catheter shaft 30 may be formed from any suitable shaft material. Examples include, but are not limited to, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the shaft material mixture can contain up to about 6 percent LCP. In some embodiments, the catheter shaft 30 is formed from a polyamide, for example Grilamid® which is commercially available from EMS-Grivory.

In an example, the inner surface of at least one of the proximal and distal waist portions 16a, 16b are thermally bonded to an outer surface of a distal portion of the catheter shaft 30 prior to bonding of the fiber braid 20 to the proximal and distal waist portions 16a, 16b. As used herein, thermal bonding refers to the melting of materials or a portion thereof by applying heat, laser, welding or some combination thereof, to obtain a mixing or bonding of the materials at the material interface. An inner surface of the fiber braid 20 is then adhesively bonded to an outer surface of the proximal and distal waist portions 16a, 16b.

A suitable adhesive may be employed for bonding the fiber braid 20 to the proximal and distal waist portions 16a, 16b and include, but are not limited to, for example, thermoset adhesives that suitably cure either via a chemical reaction or irradiation. Specific examples of suitable thermoset adhesives include moisture cure and radiation cure such as ultraviolet (UV) radiation cure, e-beam, and the like. In some embodiments, the adhesive is a thermoset cyanoacrylate adhesive. A particular example is Loctite 4011 available from Henkel Adhesives.

Figure 2:
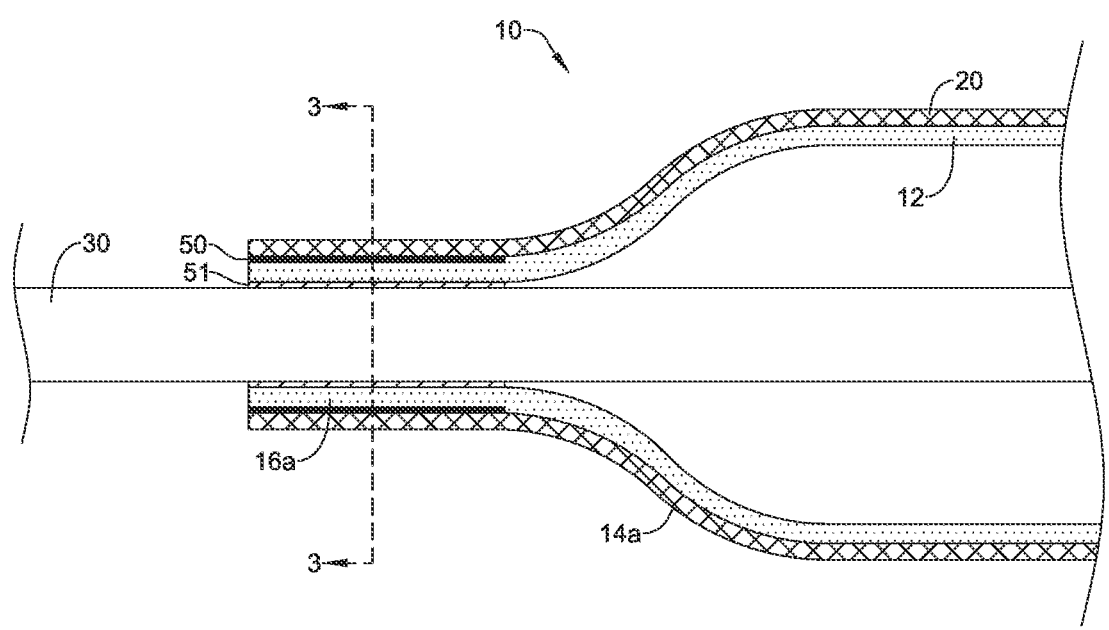
FIG. 2 is a partial cross-sectional side view of an example medical device.

FIG. 2 is a partial cross-section of the balloon 10 disposed on the distal portion of the catheter shaft 30 wherein an inner surface of the fiber braid 20 is adhesively bonded to an outer surface of the proximal waist portion 16a and an inner surface of the proximal waist portion 16a is thermally bonded to an outer surface of a distal portion of the catheter shaft 30. This is also illustrated in cross-section in FIG. 3 which is taken at section 3-3 from FIG. 2. An adhesive 50 may be disposed between the outer surface of the proximal waist portion 16a and the inner surface of the fiber braid 20. The proximal waist portion 16a may be secured to the catheter shaft 30 with another type of bond such as, for example, a thermal bond which is shown schematically in FIGS. 2 and 3 as a thermal bond region 51. As indicated above, a coating (not shown) may be disposed along the exterior of the fiber braid 20.

Figure 4:
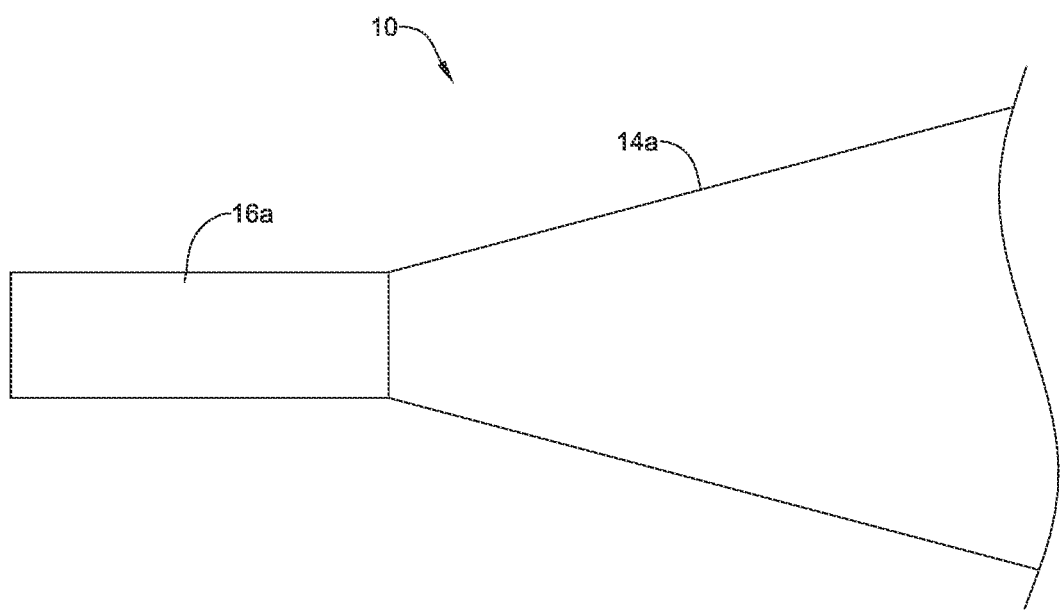
FIGS. 4-10 illustrate an example manufacturing process for an example medical device.
Figure 5:
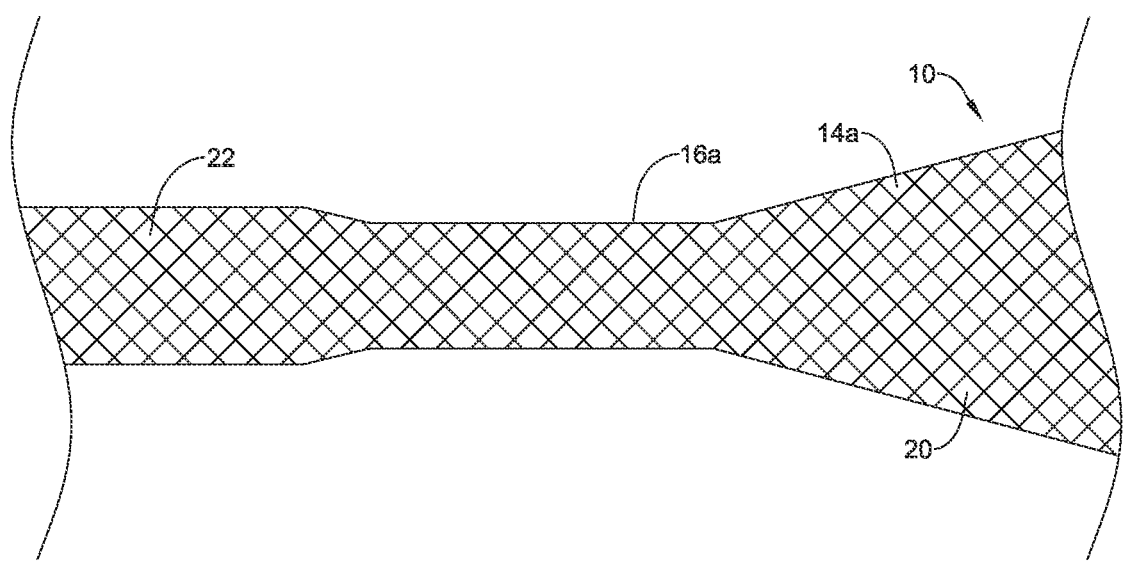
Figure 6:
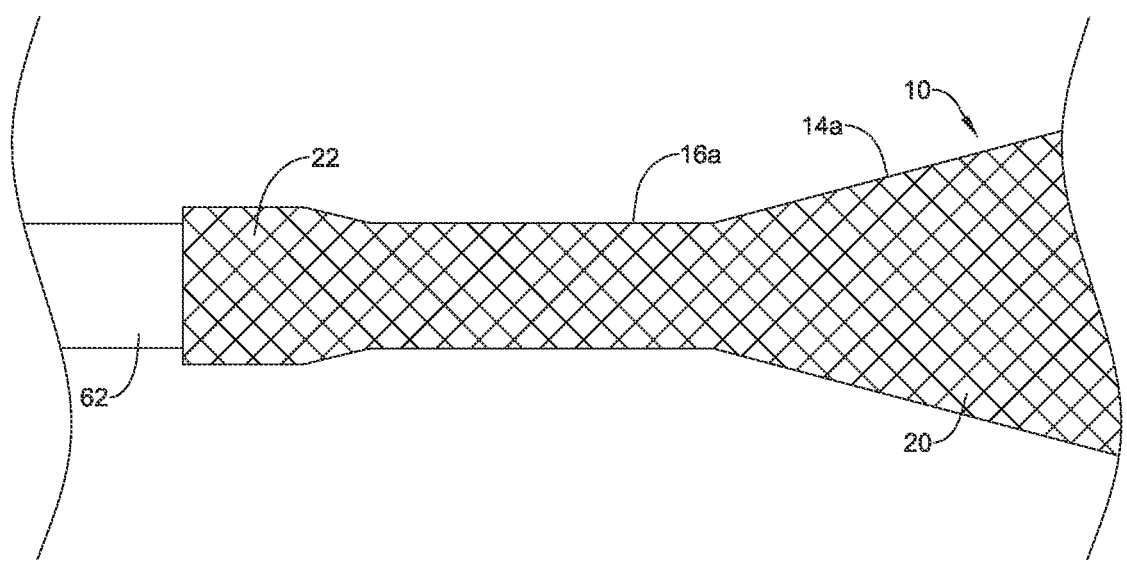

FIGS. 4-10 illustrate an example method of manufacturing the balloon catheter 11 and/or other balloon catheters. FIG. 4 is a side view of a portion of the balloon 10 having the proximal cone portion 14a and the proximal waist portion 16a prior to application of the fiber braid 20 and prior to disposition on the catheter shaft 30. FIG. 5 is a side view of the balloon 10 having the proximal cone portion 14a and the proximal waist portion 16a after application of the fiber braid 20 onto the balloon 10. In this embodiment, the fiber braid 20 extends beyond the proximal waist portion 16a of the balloon 10 resulting in a portion 22 of fiber braid 20 that is unsupported by the balloon 10. In this case, the proximal waist portion 16a of the balloon 10 is shown and the unsupported portion 22 of the fiber braid 20 is shown extending proximally beyond the proximal end of the proximal waist portion 16a. A mandrel 62 (not shown in FIG. 5, can be seen in FIG. 6) may be placed adjacent to or otherwise underneath the unsupported portion 22 of the fiber braid 20. The unsupported portion 22 of the fiber braid 20 may be trimmed to a desired length as shown in FIG. 6.

Figure 7:
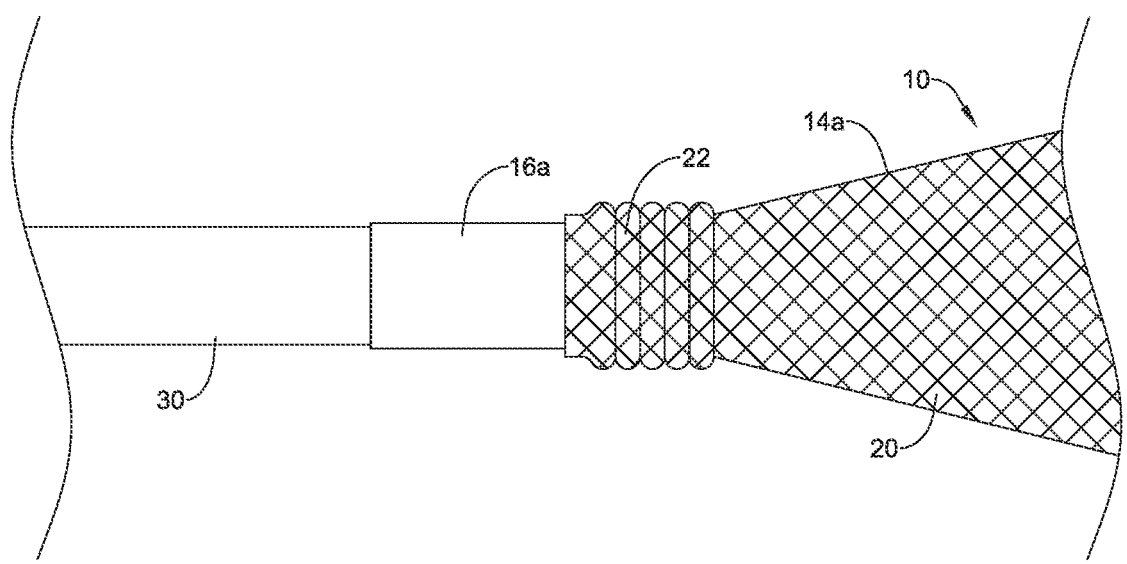
Figure 8:
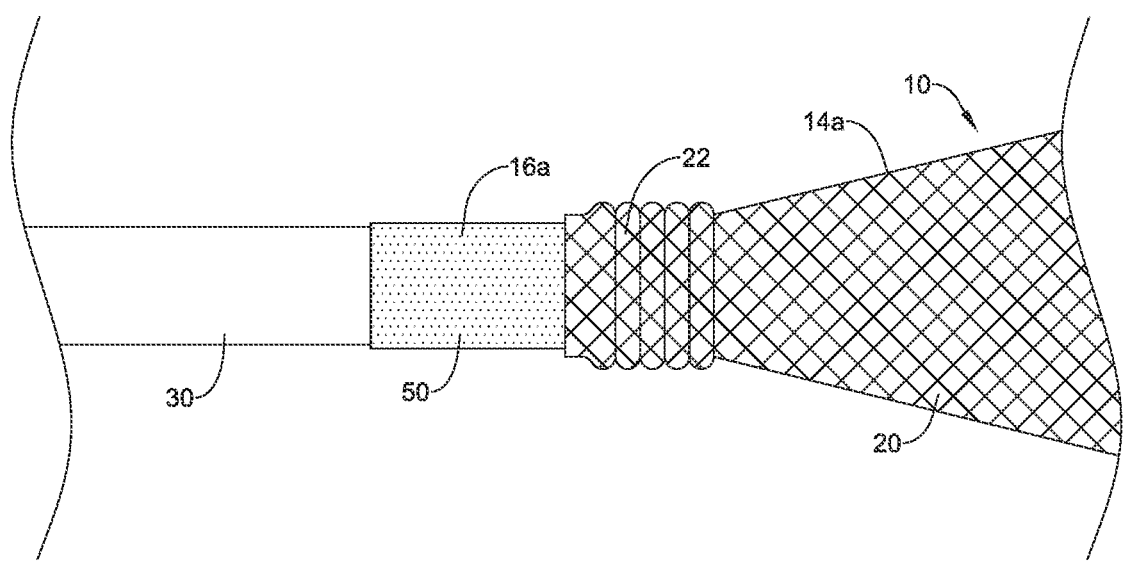
Figure 9:
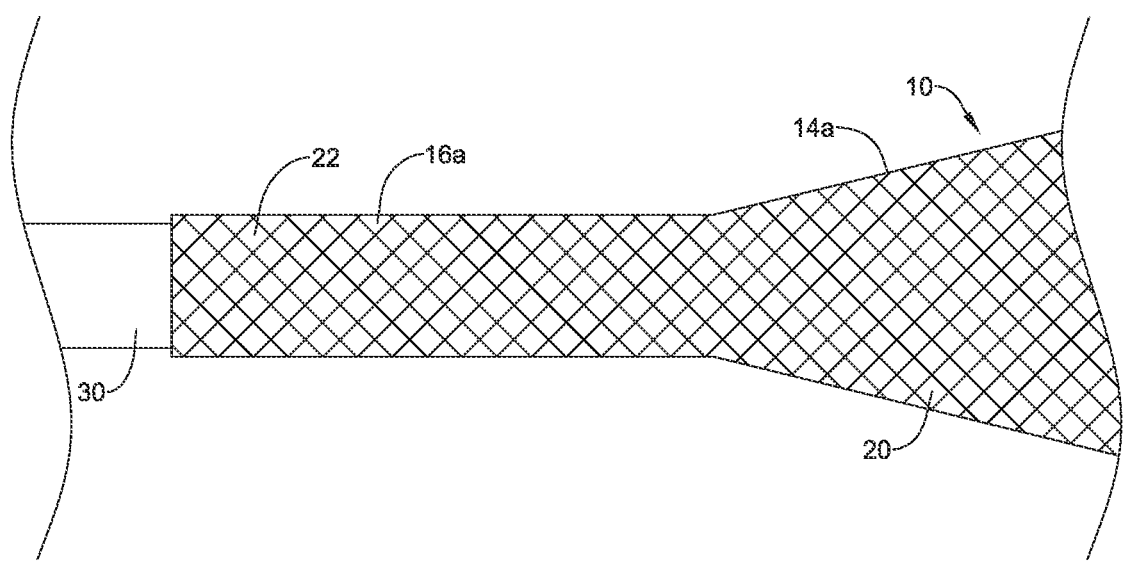
Figure 10:
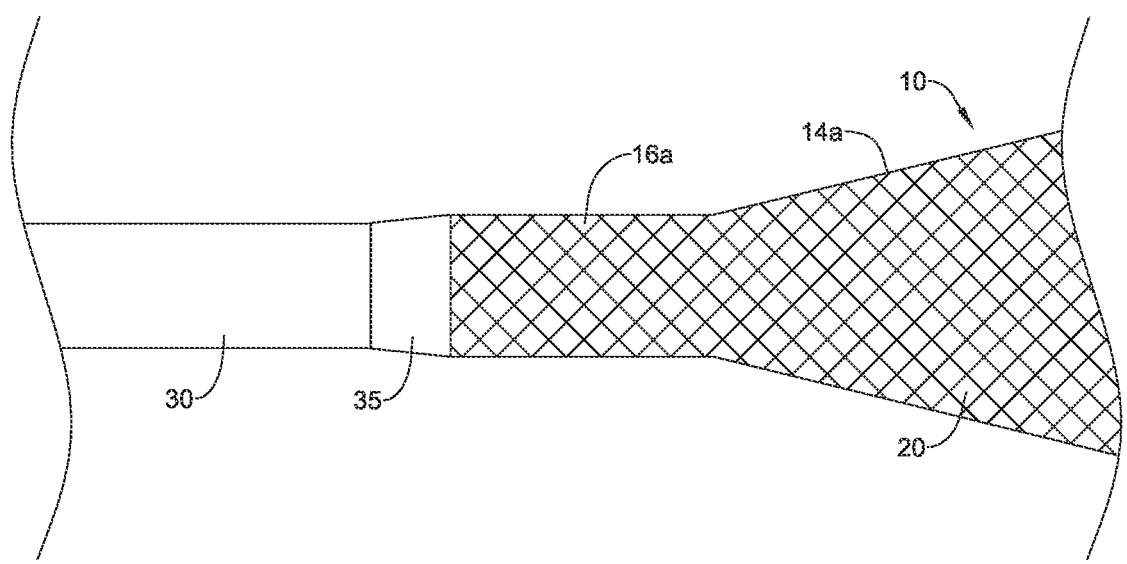
Figure 11:
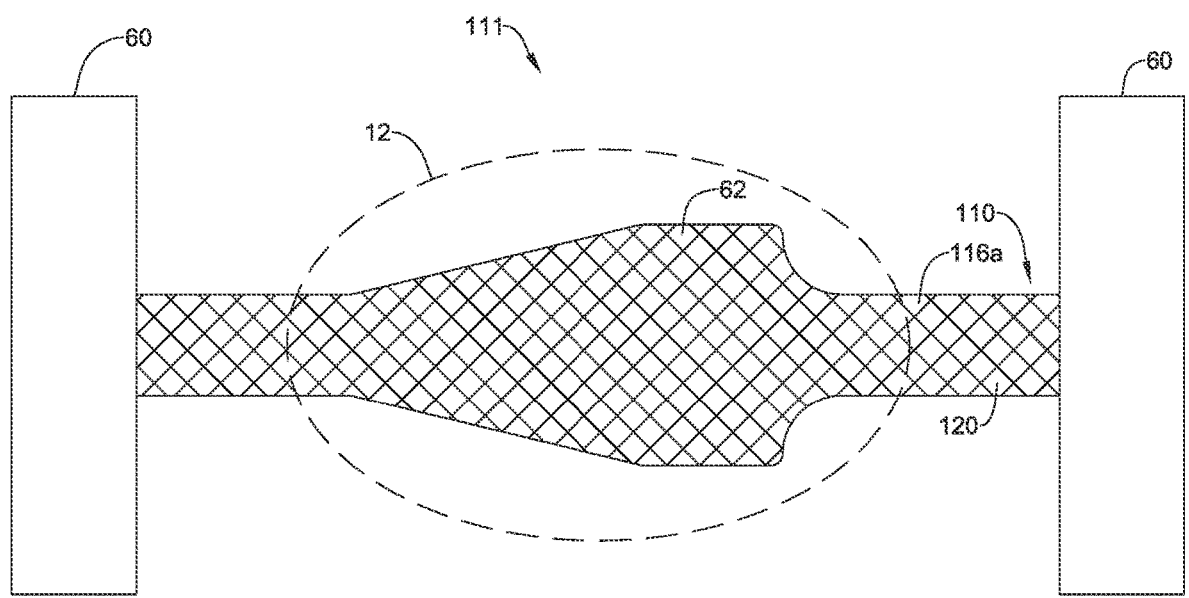
FIGS. 11-21 illustrate an example manufacturing process for an example medical device.

The temporarily unsupported portion 22 of the fiber braid 20 (and a portion of the fiber braid 20 that is supported by the proximal waist portion 16a) is then retracted, pushed back, otherwise rolled back to expose a portion of the proximal waist portion 16a to allow for thermal bonding of the balloon of the proximal waist portion 16a to the catheter shaft 30 shown in FIG. 7. In this example, the mandrel 62 is removed and the catheter shaft 30 is disposed within the proximal waist portion 16a. Heat can be applied to thermally bond the proximal waist portion 16a to the catheter shaft 30. After thermal bonding, adhesive 50 is then applied to the exposed proximal waist portion 16a as shown in FIG. 8. The fiber braid 20 (including portion 22) is then moved proximally to cover the proximal waist portion 16a as shown in FIG. 9 and the fiber braid 20 is now bonded to the proximal waist portion 16a via the adhesive (and the proximal waist portion 16a is thermally bonded to the catheter shaft 30). In some instances, the fiber braid 20 (e.g., the unsupported portion 22 of the fiber braid 20) may be trimmed to a desired length and a fillet application of adhesive 35 may be applied at the proximal bond site as shown in FIG. 10.

This method preserves the molecular orientation of the fiber braid 20 by avoiding application of heat which may adversely affect some properties of the balloon 10 such as tensile and burst pressure data.

In at least some instances, the balloon catheter 11 may be formed using a suitable process. For example, the catheter shaft 30 may be formed by bonding an inner and an outer catheter shaft assembly having a dual lumen shaft formed from Grilamid®. A balloon parison (tubular member) formed of Pebax® 7033 having an 8 mm diameter may be stretched, placed in a balloon mold and formed by radial expansion. The tubes may alternatively have 4 mm or 12 mm diameters. The parison may be stretched at a tube stretch ratio of 3.0. The raw tube had an inner diameter (ID) of 0.0551" and an outer diameter (OD) of 0.0708". The stretched tube may have an ID of 0.056" and an OD of 0.059". A mandrel may be installed and the balloon parison may be inflated to 13 psi to form the balloon 10. The balloon 10 may be plasma treated with oxygen, and dip coated with 2.5% solids Lubrizol SG 60D thermoplastic polyurethane in a cosolvent blend of 50% toluene/50% tetrahydofuran. The plasma treatment may be conducted in a Nordson-March Plasma Chamber at a 100 sccm flow rate, base pressure 100 mtorr, 250 Watts, 90 Seconds times four cycles. The coating thickness may be about 4 µm. The dipping process may take up to four repeat cycles to achieve the desired thickness with 10 minutes in between each cycle at a dip down and up speed of 50 inches/minute with a hold time of 2 seconds in a 100 mL graduated cylinder. The balloon 10 may then braided with an ultra high molecular weight, highly oriented polyethylene (UHMWPE) fiber braid 20 and again plasma treated and dip coat braided balloon in 50:50 toluene:THF solvent with 2.5% solids Lubrizol SG 60D TPU to a thickness of 4 µm. The proximal and distal waist portions 16a, 16b may be trimmed, and the balloon 10 may be installed onto the inner and outer shaft assembly of the catheter shaft 30. The portion of the fiber braid 20 located on the proximal waist and distal waist portions 16a, 16b may be moved distally from each waist enough to enable thermal bonding of the proximal waist and distal waist portions 16a, 16b to inner/outer shafts of the catheter shaft 30. A distal tip can optionally be installed at this point, and the fiber braid 20 may be moved back over the proximal and distal waist portions 16a, 16b (e.g., where thermal bonds are present between the proximal and distal waist portions 16a, 16b and the catheter shaft 30), and adhesively bonded to the proximal and distal waist portions 16a, 16b of the balloon 10.

Figure 12:
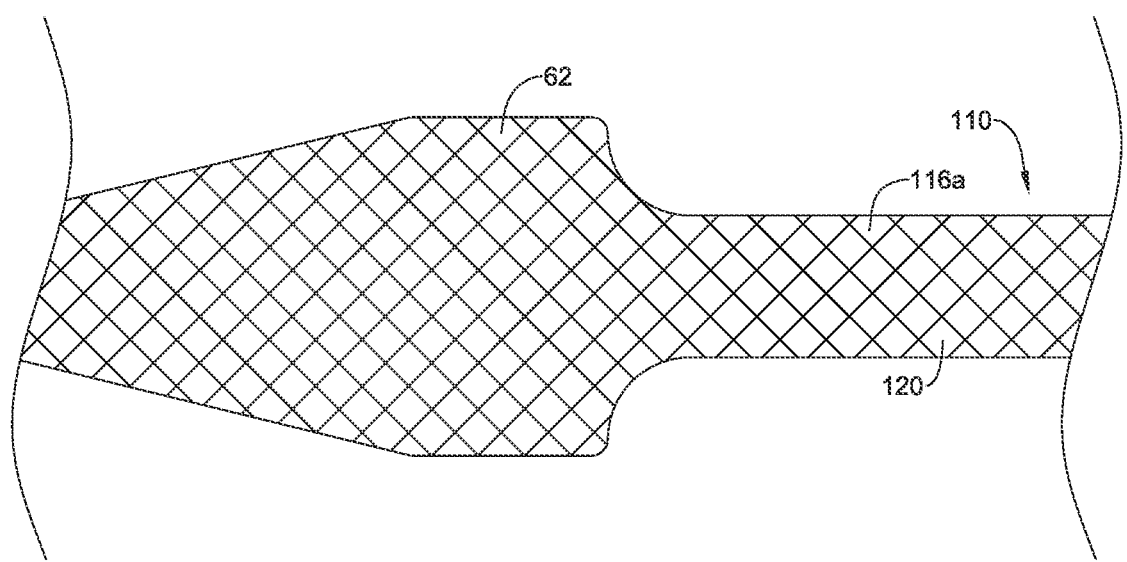

FIGS. 11 through 21 illustrate an alternative example method of making another example balloon catheter 111 that may be similar in form and function to other balloons catheters 111 disclosed herein. The process may utilize a removable mandrel 62 that may be positioned adjacent a proximal waist portion 116a of a balloon 110. The mandrel 62 and the balloon catheter 111 may be placed in a balloon holder 60 as shown schematically in FIG. 11 for waist trimming. In at least some instances, the mandrel 62 has a flared end that can be positioned adjacent to the proximal waist portion 116a to prevent the waist cutting assembly from nicking the catheter shaft 130 (not shown in FIG. 11, can be seen in FIG. 13). FIG. 12 is a view of the flared end of the mandrel 62 adjacent to the proximal waist portion 116a. The flared end may be formed integrally with the mandrel 62 or a washer or similar structure may be disposed thereon.

Figure 13:
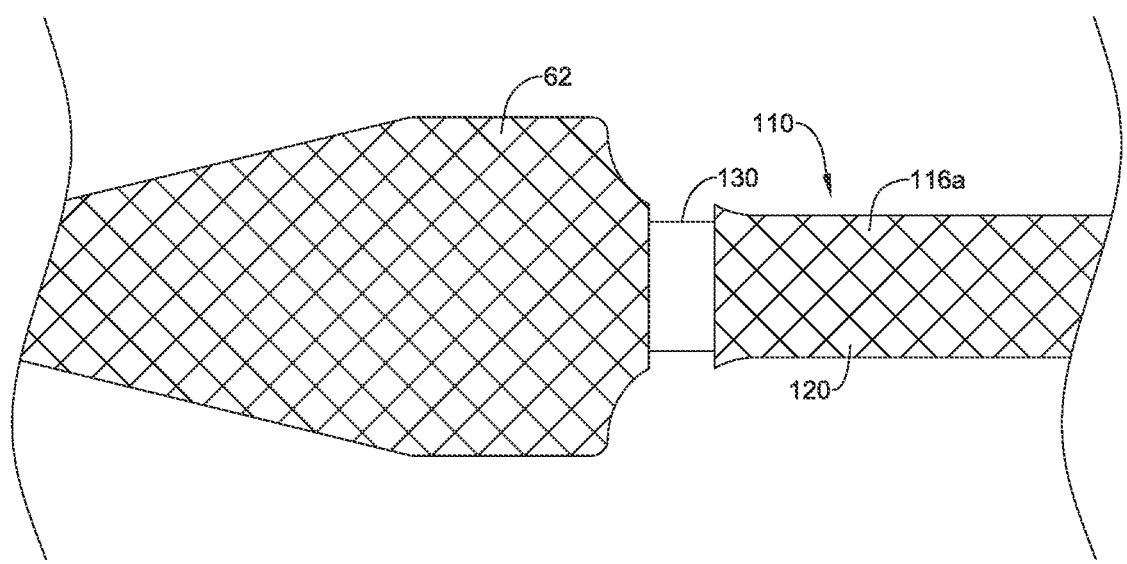
Figure 14:
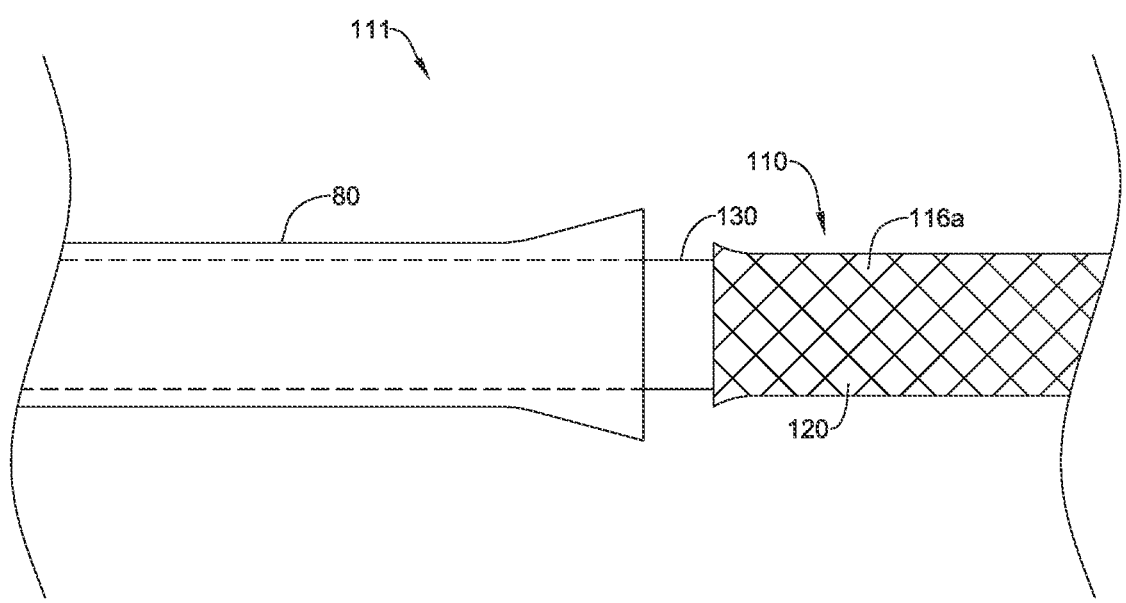
Figure 15:
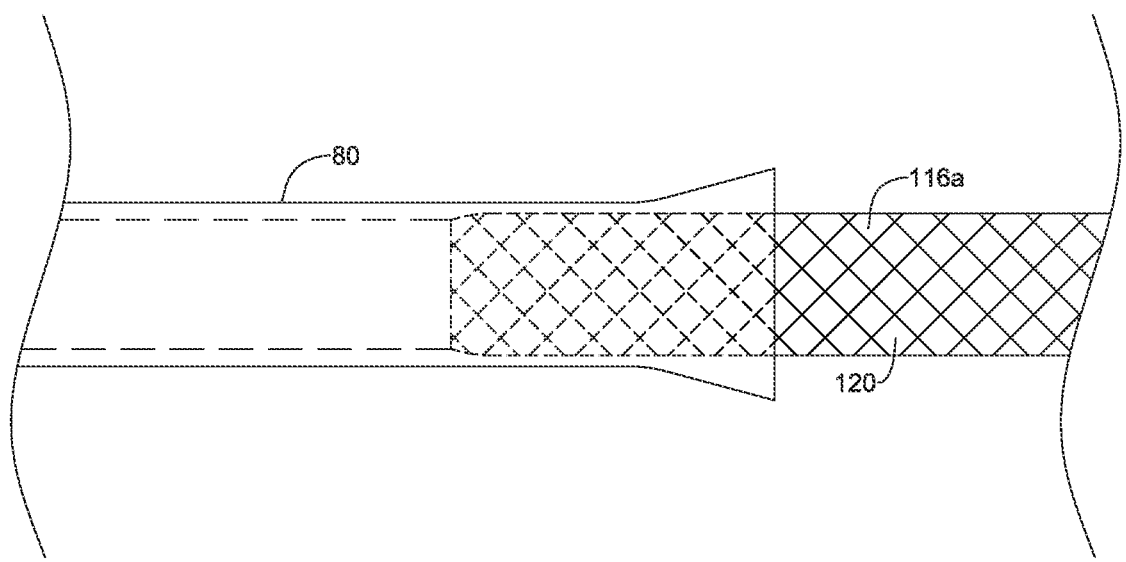

The proximal waist portion 116a may then trimmed from the fiber braid 120 at the mandrel 62 using a cutting member as shown in FIG. 13. The balloon catheter 111 is then removed from the balloon holder 60. A balloon protector 80 can be slid in a distal direction over the proximal end of the catheter shaft 130 and over the proximal waist portion 116a as illustrated in FIGS. 14 and 15.

Figure 16:
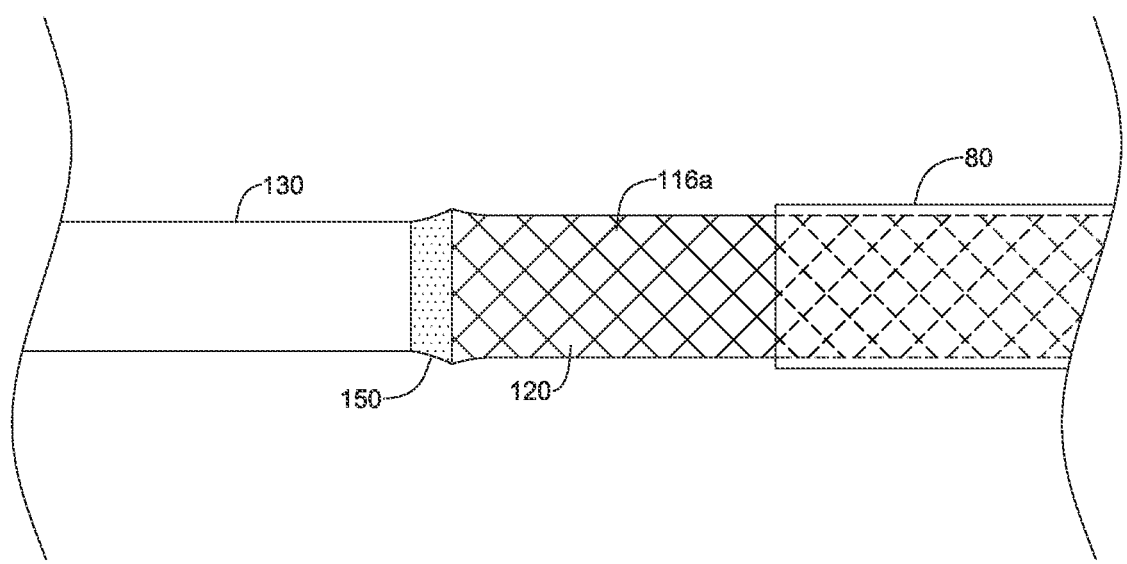
Figure 17:
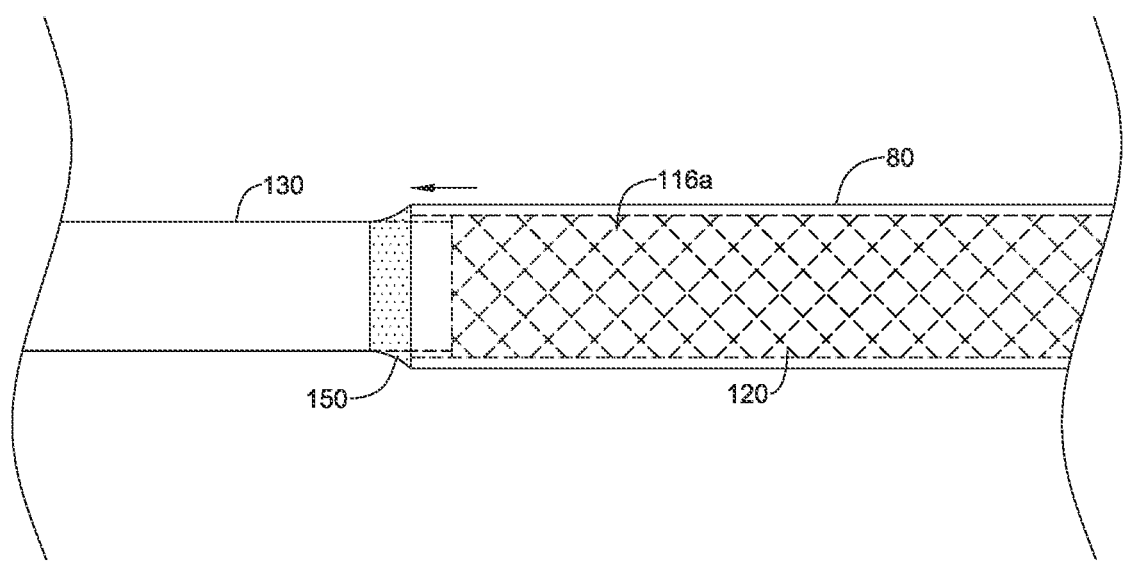
Figure 18:
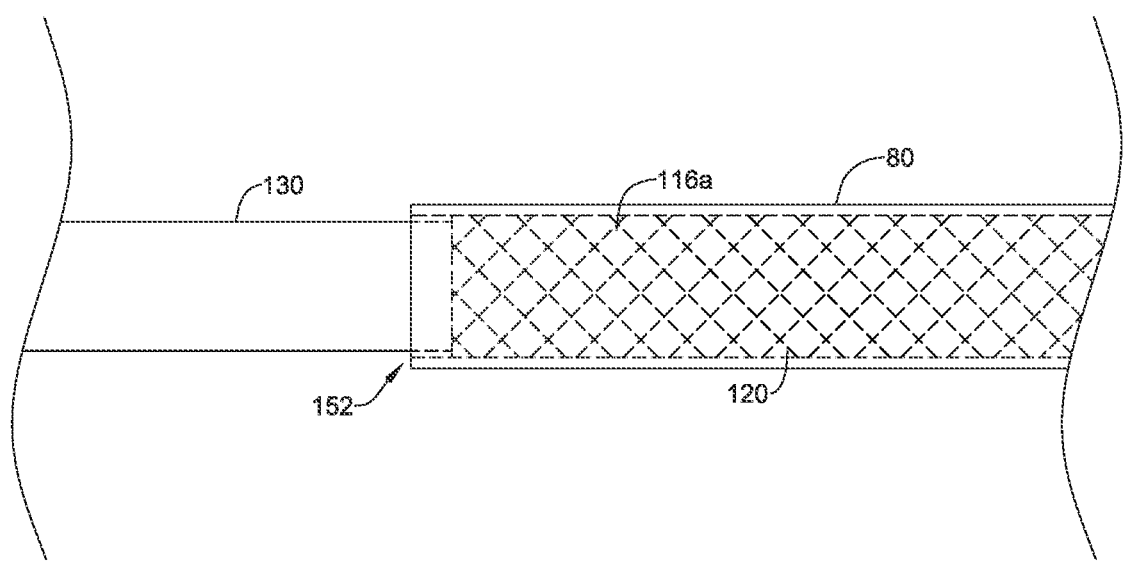
Figure 19:
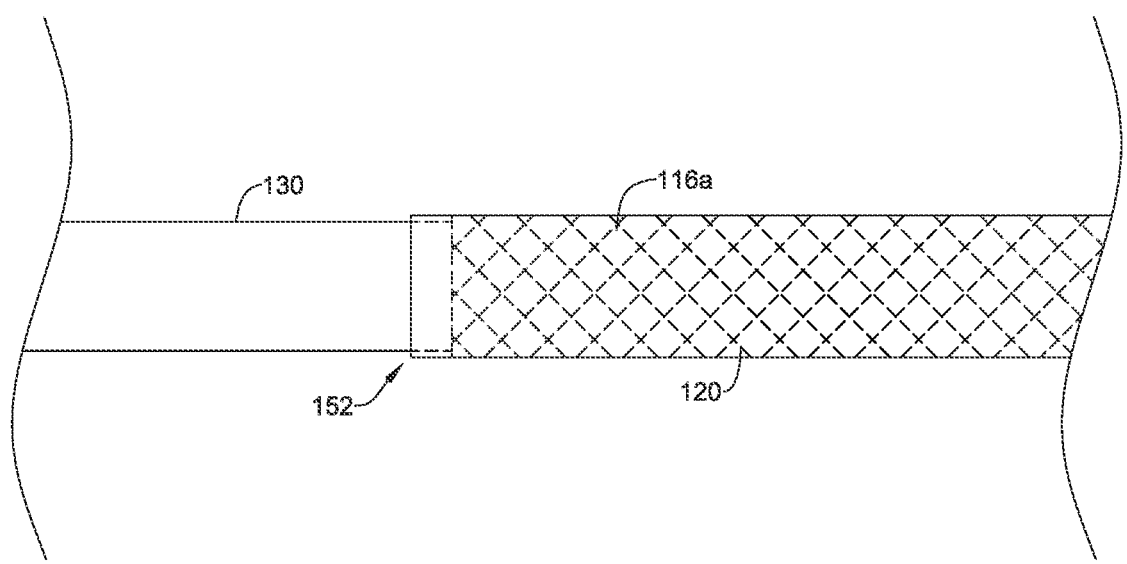
Figure 20:
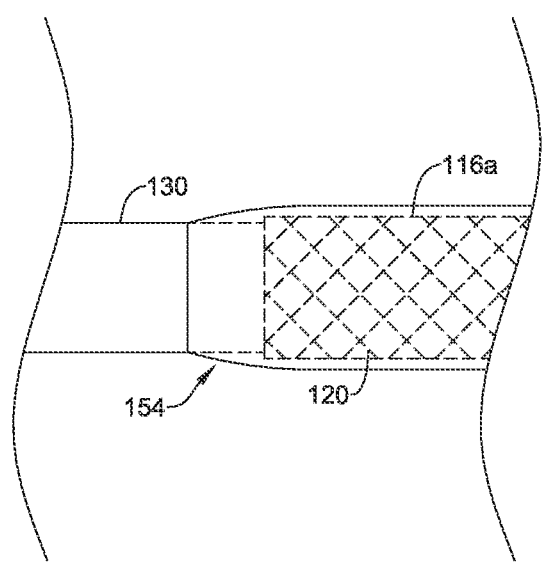

Adhesive 150 may be applied at the proximal portion of the proximal waist portion 116a. The flared portion of the mandrel 62 results in the fiber braid 120 having a slightly flared end where the fiber braid 120 terminates at the proximal portion of the proximal waist portion 116a, which also allows adhesive to seep below the fiber braid 120 onto the unexposed proximal waist portion 116a as shown in FIG. 16. The balloon protector 80 is then slid proximally over the proximal waist portion 116a and the catheter shaft 130 which squeezes out excess adhesive 150 as shown in FIGS. 17 and 18. The adhesive 150 may be a thermoset adhesive as discussed above. In some instances, the adhesive is an ultraviolet (UV) cure adhesive. In this embodiment, the balloon protector 80 is selected to as to be transparent to UV radiation, such as a clear Teflon material so that the adhesive 150 can be cured with the balloon protector 80 in place. The balloon protector 80 may be removed as shown in FIG. 19. The cured adhesive may leave a step 152 at the proximal end of the fiber braid 120 on the proximal waist portion 116a. A fillet 154 of adhesive may be applied to smooth out the step 152 as shown in FIG. 20 and smoothed out over the proximal end of the fiber braid 120. The adhesive fillet 154 can then also be UV cured.

Figure 21:
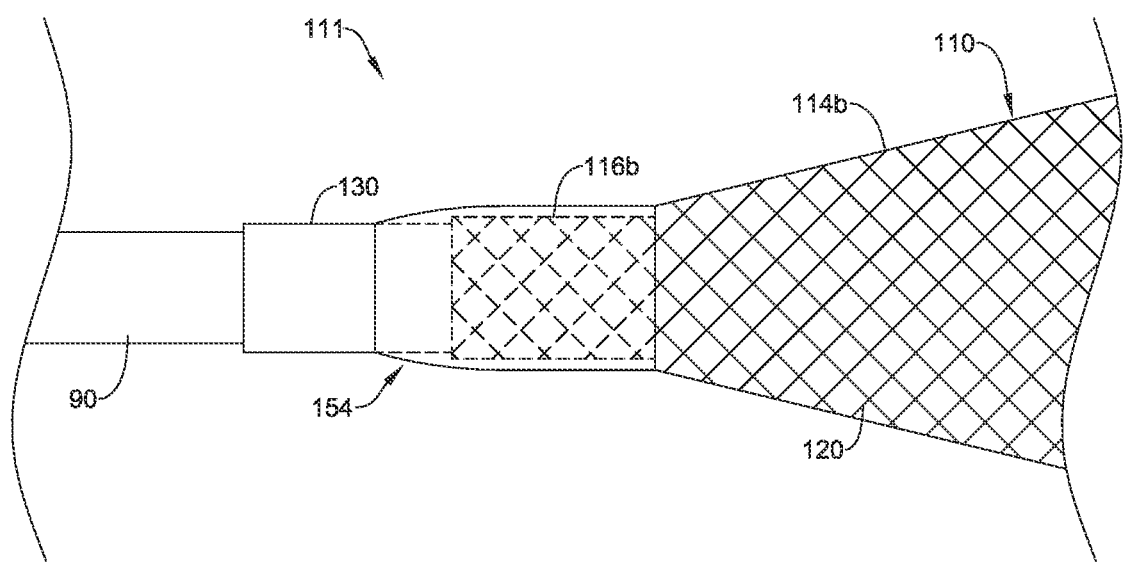

FIG. 21 is a side view of the distal end of the balloon catheter 111 illustrating the catheter shaft 130, the adhesive fillet 154, the proximal waist portion 116b, and the proximal cone portion 114b of the balloon 110. The assembly is shown disposed on a guidewire 90. This may also be a removable mandrel or other tubular member.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

The invention claimed is:

1. A method of making a catheter assembly, the method comprising:
   disposing a fiber braid about a balloon, the balloon comprising a cone portion, a waist portion and a body portion, an end of the fiber braid being terminated at a predetermined point relative to the waist portion;
   disposing the balloon on a catheter shaft;
   applying heat to at least a portion of the waist portion to thermally bond an inner surface of the waist portion to an outer surface of the catheter shaft; and
   after thermally bonding the waist portion and the catheter shaft, then applying adhesive to bond an inner surface of the fiber braid to the outer surface of the waist portion;
   wherein a first section of the fiber braid is supported by the waist portion and a second section of the fiber braid extends beyond the waist portion in a direction away from the body portion such that the second section is unsupported by the waist portion, wherein applying heat to the waist portion includes first retracting at least the second section of the fiber braid and a region of the first section of the fiber braid toward the body portion to expose at least some of the waist portion before thermally bonding the waist portion to the catheter shaft.

2. The method of claim 1, further comprising trimming the end of the fiber braid to a predetermined length.

3. The method of claim 2, further comprising applying additional adhesive to the end of the fiber braid to provide a smooth transition from the fiber braid to the catheter shaft, and curing the additional adhesive.

4. The method of claim 1, wherein the predetermined point relative to the waist portion is a point beyond the waist portion in a direction away from the body portion.

5. The method of claim 1, wherein applying adhesive includes applying adhesive to the exposed waist portion, then moving the second section of the fiber braid back over the waist portion, and curing the adhesive.

6. The method of claim 1, wherein disposing the balloon on the catheter shaft includes welding the waist portion to the catheter shaft, braiding the fiber braid over the balloon and the catheter shaft, trimming the fiber braid at a predetermined location, and applying the adhesive to the waist portion, to the inner surface of the fiber braid at the waist portion at the predetermined location, or both.

7. The method of claim 1, wherein the fiber braid comprises a molecularly oriented ultra high molecular weight polyethylene.

8. The method of claim 1, wherein the adhesive is a non-heat curing adhesive.

9. The method of claim 8, wherein the non-heat curing adhesive is an ultraviolet (UV) curing adhesive, wherein adhesively bonding the inner surface of the fiber braid to the outer surface of the waist portion includes subjecting the waist portion to UV light.

10. A method of making a catheter assembly, the method comprising:
disposing a fiber braid about a balloon, the balloon comprising a body portion, a waist portion, and a cone portion disposed between the body portion and the waist portion, an end of the fiber braid being terminated at a predetermined point relative to the waist portion;
disposing the balloon on a catheter shaft;
retracting at least a section of the fiber braid toward the body portion to expose a section the waist portion;
applying heat to at least the exposed section of the waist portion to create a thermal bond between an inner surface of the waist portion and an outer surface of the catheter shaft; and
after creating the thermal bond, then moving the retracted section of the fiber braid back over the waist portion, and adhesively bonding an inner surface of the fiber braid to the outer surface of the waist portion.

11. The method of claim 10, wherein the fiber braid is terminated at a point beyond the waist portion in a direction away from the body portion, resulting in an unsupported section of the fiber braid unsupported by the waist portion.

12. The method of claim 11, wherein retracting at least a section of the fiber braid includes retracting the unsupported section of the fiber braid.

13. The method of claim 10, wherein after adhesively bonding the inner surface of the fiber braid to the outer surface of the waist portion, the method further comprises applying additional adhesive to the end of the fiber braid to provide a smooth transition from the fiber braid to the catheter shaft, and curing the additional adhesive.

14. The method of claim 10, wherein the fiber braid comprises a molecularly oriented ultra high molecular weight polyethylene.

15. The method of claim 10, wherein adhesive bonding includes applying a non-heat curing adhesive.

16. The method of claim 15, wherein the non-heat curing adhesive is an ultraviolet (UV) curing adhesive, wherein adhesively bonding the inner surface of the fiber braid to the outer surface of the waist portion includes subjecting the waist portion to UV light.

17. A method of making a catheter assembly, the method comprising:
disposing a fiber braid about a balloon, the balloon comprising a cone portion, a waist portion and a body portion, an end of the fiber braid being terminated and flared at a predetermined point relative to the waist portion;
disposing the balloon on a catheter shaft;
sliding a balloon protector distally over the waist portion of the balloon toward the body portion, exposing a section of the waist portion;
applying a non-heat curing adhesive to a proximal region of the exposed section of the waist portion and allowing the adhesive to flow under the flared end of the fiber braid;
sliding the balloon protector proximally over the waist portion to squeeze out excess adhesive; and
curing the adhesive.

18. The method of claim 17, wherein the non-heat curing adhesive is a UV curing adhesive, and the balloon protector is transparent to UV radiation.

19. The method of claim 17, wherein curing the adhesive results in a step between the end of the fiber braid and the waist portion, wherein the method further comprises adding additional adhesive to smooth out the step.

* * * * *